(12) United States Patent
Tomono et al.

(10) Patent No.: US 6,448,048 B1
(45) Date of Patent: Sep. 10, 2002

(54) METHOD FOR EFFECTING SITE-DIRECTED MUTAGENESIS

(75) Inventors: Jun Tomono, Muko; Akihiko Kita, Mie-gun; Susumu Tsunasawa, Otsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/214,146

(22) PCT Filed: Jul. 7, 1999

(86) PCT No.: PCT/JP97/02355

§ 371 (c)(1),
(2), (4) Date: Dec. 29, 1998

(87) PCT Pub. No.: WO98/02535

PCT Pub. Date: Jan. 22, 1998

(30) Foreign Application Priority Data

Jul. 11, 1996 (JP) ............................................. 8-202851

(51) Int. Cl.[7] .......................... C12N 15/64; C12Q 1/68; C12P 19/34; C07H 21/02; C07H 21/04
(52) U.S. Cl. ........................ 435/91.41; 435/6; 435/91.1; 435/91.2; 435/91.42; 536/23.1; 536/24.3; 536/24.33
(58) Field of Search ............................... 435/69.1, 69.2, 435/71.1, 71.2, 91.1, 91.2, 91.4, 91.41, 91.42, 91.5, 440, 471, 476, 488, 183; 536/24.33, 24.3, 23.1, 25.3; 436/94

(56) References Cited

U.S. PATENT DOCUMENTS 5,512,463 A 4/1996 Stemmer .................. 435/91.2
5,702,931 A * 12/1997 Andrews et al. ......... 435/172.3

FOREIGN PATENT DOCUMENTS

JP 07289262 A * 11/1995

OTHER PUBLICATIONS

Shen et al., A marker-coupled method for site-directed mutagenesis. Gene, 103, 73–77, 1991.*
Hashimoto–Gotoh et al., An oligodeoxyribonucleotide–directed dual amber method for site–directed mutageneis. Gene, 152, 271–275, 1995,*
Jones et al., A rapid method for recombination and site–specific mutagenesis by placing homologous ends on DNA using polymerase chain reaction. Biotechniques, 10, 62–66.*
Prodromou et al., Recursive PCR: a novel technique for total gene synthesis. Protein engineering, 5, 827–829, 1992.*
Pharmacia Biotech Catalgue (1996), p. 132. Published by Pharmacia Biotech Inc., 800 Centennial Ave., P. O. Box, Piscataway, NJ 08855–1327.*
Hashimoto–Gotoh et al., Gene, vol. 152, pp. 271–275, 1995.*
Stratagene Catalog 1988 (Published by Strategene, 11011 North Torrey Pines Road, La Jolla, CA 92037), p. 39, 1988.*
Gene, vol., 103, Tong–Jian Shen et al, (1991) pp. 73–77.
Current Genetics, vol. 28, Eckhard Boles et al, (1995) pp. 197–198.
Stemmer et al Biotechnique No. 146, vol. 13, No. 2 (1992) pp. 214–220.
Nucleic Acids Research, vol. 12, No. 24 Kramer et al, (1984) pp. 9441–9456.
Analytical Biochemistry 200, Deng et al, (1992), pp. 81–88.
Gene, vol. 102, Ito, et al, (1991), pp. 67–70.
Kunkee Proc. Natl. Acad. Sci. U.S.A., vol. 82. (Jan. 1985), pp. 488–492.

* cited by examiner

Primary Examiner—Ethan C. Whisenant
Assistant Examiner—Frank Lu
(74) Attorney, Agent, or Firm—Birch, Stewart, Kolasch & Birch, LLP (57) ABSTRACT

A method for performing site-directed mutagenesis characterized in that the method includes the step of carrying out PCR by the use of a double-stranded DNA vector having one or more amber codons, the vector resulting from insertion of a target DNA fragment for site-directed mutagenesis, and at least two kinds of selection primers; and a kit for site-directed mutagenesis for use in the above method, characterized in that the kit includes amber codon reversion primers. According to the present invention, there can be provided a method for performing site-directed mutagenesis and a kit, which is useful for genetic engineering or protein engineering, more simply and rapidly. By using the method and the kit of the present invention, it is possible to efficiently obtain a mutation-introduced gene at the desired position by simply transforming a host with a PCR product obtained by PCR.

15 Claims, 2 Drawing Sheets

METHOD FOR EFFECTING SITE-DIRECTED MUTAGENESIS

This application is the national phase under 35 U.S.C. §371 of prior PCT International Application No. PCT/JP97/02355 which has an International filing date of Jul. 7, 1999 which designated the United States of America.

TECHNICAL FIELD

The present invention concerns a method for performing site-directed mutagenesis used in genetic engineering techniques, more easily and efficiently, and a kit for the use in the above method.

BACKGROUND ART

In the field of genetic engineering, recently, it is often difficult to obtain a gene product in large amounts while solely relying on techniques of cloning gene to express, and successful cases are few. For this reason, in order to increase a level of expression of a product of a cloned gene, a technique for coinciding a frame and a technique for altering base sequences near the initiation codon without altering amino acid sequences (silent mutation) are minimally required techniques. In addition, in order to carry out cloning of genes and produce more useful protein as a protein to be expressed, a technique is important and essential, which alters the base sequence of a corresponding codon to delete or substitute amino acids and thereby modifies specificities of the protein, such as optimal pH, stability, substrate specificity, Km value, and the like, in the cases where the protein is an enzyme.

As described above, a method for changing a particular base sequence in a cloned gene as desired, i.e. site-directed mutagenesis, is essential to carry out structural and functional analyses of various regulatory regions on genes including RNA, and protein engineering applications using recombinant DNA techniques. In addition, in the research field of protein engineering, a method for performing site-directed mutagenesis is more important, in a view of more rapid and accurate research by introduction of mutations and elimination at the DNA level.

Conventionally, a method for performing site-directed mutagenesis comprises, for instance, the following procedures:

(1) First, a desired DNA to be mutation-introduced is inserted to a vector. Thereafter, the complementary strand of the desired DNA is dissociated by heat-denaturation, in the case of using a double-stranded plasmid DNA, or a M13 phage vector is used to prepare a single-stranded DNA;

(2) An oligonucleotide designed to introduce a desired mutation (mutagenic primer) is annealed with the above single-stranded DNA. Thereafter, a complimentary strand DNA is synthesized in vitro system by a reaction of DNA polymerase and DNA ligase;

(3) *Escherichia coli* is transformed with the DNA obtained in the above item (2), and then a clone in which a mutation is introduced is selected.

However, since a ratio of a mutant to a parent DNA is extremely low in the case of carrying out only the above procedures, it is necessary to efficiently select a clone resulting from annealing to a mutagenic primer. Therefore, in the step of the above item (3), there is employed a system for selective removal so that a clone harboring the parent DNA does not grow.

Examples of such system are a method utilizing amber mutation (amber codon) [*Nucleic Acids Research*, 12, No. 24, pp.9441–9456 (1984)]; a method utilizing restriction endonuclease site [*Analytical Biochemistry*, 200, pp.81–88 (1992); Gene, 102, pp.67–70 (1991)]; and a method utilizing dut (dUTPase) mutation and ung (uracil DNA glycosilase) mutation [*Proceedings of the National Academy of Sciences of the USA*, 82, pp.488–492 (1985)], etc. However, in these methods of mutagenesis, their procedures are complicated, and much time is consumed. In addition, in these methods, a proportion of obtaining desired clones in which a mutation is introduced is low.

On the other hand, a method of site-directed mutagenesis described in Japanese Patent Laid-Open No. Hei 7-289262 is a method utilizing amber mutation using DNA polymerase and DNA ligase. As compared to the above methods, although in the method described in Japanese Patent Laid-Open No. Hei 7-289262, mutants can be produced at a high efficiency, the two-step transformation into *Escherichia coli* is necessary, thus hampering simple operation for practically purposes.

In recent years, methods for site-directed mutagenesis based on the wide-spread use of PCR techniques have been developed.

For example, there has been known a method is known, the method comprising the steps of synthesizing a DNA strand to be mutation-introduced using three or more kinds of primers, the primers including a mutagenic primer; thereafter cutting out a DNA strand with restriction endonucleases and then ligating to another vector the resulting DNA strand in which a mutation is expected to be introduced; and transforming a host *Escherichia coli* with the resulting vector. In addition, Quik Change™ Site-Directed Mutagenesis Kit, manufactured by Stratagene, can be used to obtain a mutation-introduced DNA by means of synthesizing a strand with PCR or DNA polymerase from *Pyrococcus furiosus* using two kinds of complementary mutagenic oligonucleotides (mutagenic primers), the oligonucleotides being capable of hybridizing to double-stranded DNA to which mutation is to be introduced, thereafter, digesting with restriction endonuclease DpnI the resulting strand without mutation, and then transforming a host *Escherichia coli* with resultants treated with DpnI. Furthermore, there has been known a method capable of obtaining a mutation-induced DNA comprising adding class IIS restriction endonuclease recognition site at 5'-terminal side of each two kinds of mutagenic oligonucleotides (mutagenic primers), synthesizing strands by PCR, thereafter digesting with class IIS restriction endonuclease a mutation-introduced DNA, ligating and then transforming a host *Escherichia coli* (U.S. Pat. No. 5,512,463).

As described above, the conventional method using DNA polymerase and DNA ligase necessitates such enzyme reactions and a plurality of steps of transformation for fixing mutation sites, consuming too much time, thereby making it difficult to increase efficiency. Also, in the methods utilizing amber mutation or "dut" and "ung" mutations, single-stranded DNA must be isolated. The method for removing restriction endonuclease site has drawbacks, including limited availability of restriction endonucleases.

In view of the above, a method for performing site-directed mutagenesis using the recently widely spread PCR technique has been developed and brought into actual application. However, its operation is complicated by necessitating three or more kinds of primers, including mutagenic primers, the primers including two or more kinds of mutagenic primers, and by necessitating a restriction endonuclease reaction during the operation, and other aspects. There have been other various problems including extremely reduced mutation efficiency that can result from incomplete restriction endonuclease reaction.

Therefore, an object of the invention is to provide a simple and practical method for performing site-directed mutagenesis using PCR method, and a kit for carrying out the method for performing site-directed mutagenesis.

As a result of intensive investigation to develop an efficient and simple method for performing site-directed mutagenesis, the present inventors have succeeded to obtain a clone in which a desired mutation is introduced, only once transforming *Escherichia coli* after carrying out PCR. The present invention has been completed, based on such a fact.

DISCLOSURE OF INVENTION

Accordingly, the gist of the present invention follows:

[1] a method for performing site-directed mutagenesis characterized in that the method comprises the step of carrying out PCR by the use of a double-stranded DNA vector having one or more amber codons, the vector resulting from insertion of a target DNA fragment for site-directed mutagenesis, and at least two kinds of selection primers;

[2] the method for performing site-directed mutagenesis according to the above item [1], wherein the selection primers are mutagenic primers and amber codon reversion primers;

[3] the method for performing site-directed mutagenesis according to the above item [1] or [2], characterized in that the vector carries a drug resistance gene containing one or more amber codons;

[4] the method for performing site-directed mutagenesis according to any one of the above items [1] to [3], further comprising a step of transforming a suppressor-free (Sup$^0$) host with a PCR product;

[5] the method for performing site-directed mutagenesis according to the above item [4], characterized in that the suppressor-free (Sup$^0$) host is *Escherichia coli*;

[6] a kit for site-directed mutagenesis for use in the method for performing site-directed mutagenesis according to any one of the above items [1] to [5], characterized in that the kit comprises amber codon reversion primers;

[7] the kit for site-directed mutagenesis according to the above item [6], characterized in that the kit comprises a vector having one or more amber codons;

[8] the kit for site-directed mutagenesis according to the above items [6] or [7], characterized in that the kit comprises a suppressor-free (Sup$^0$) host; and

[9] the kit for site-directed mutagenesis according to the above item [8], characterized in that the suppressor-free (Sup$^0$) host is *Escherichia coli*.

BEST MODE FOR CARRYING OUT THE INVENTION

The present invention will be explained in detail below.

The present invention is a method for performing site-directed mutagenesis characterized in that the method comprises the step of carrying out PCR by the use of a double-stranded DNA vector having one or more amber codons, the vector resulting from insertion of a target DNA fragment for site-directed mutagenesis, and at least two kinds of selection primers. As the selection primers used in the present invention, there can be used at least two kinds of primers consisting a mutagenic primer for inducing a mutation at a desired position on the gene to be mutated; and an amber codon reversion primer for reverting the amber codons, the amber codon reversion primer being arranged on the strand opposite to the mutagenic primer. The term "at least two kinds of primers" as used herein refers to the mutagenic primers and the amber codon reversion primers, and at least two kinds of selection primers as described in the present invention encompass any set of selection primers, as long as these two kinds of selection primers are included.

The double-stranded DNA vector used in the present invention which has one or more amber codons may be any vector, as long as the vector has one or more amber codons, and can be used without limitation for the method for performing site-directed mutagenesis of the present invention. In this case, it is preferred that a vector having the amber codon(s) on a drug resistance gene is used. The drug resistance gene is not particularly limited, but the kanamycin resistance gene, the chloramphenicol resistance gene, etc., for example, are preferred. In other words, vectors having one or more amber codons on a drug resistance gene, such as the kanamycin or chloramphenicol resistance gene, can be preferably used. For instance, pKF19k (manufactured by Takara Shuzo Co., Ltd.) can be used. It is also possible to prepare a cassette having amber codons and then introduce the cassette into a vector. By the use of such a vector, it is easy to confirm the reversion of amber codons on the drug resistance gene simply by introducing the PCR product into a suppressor-free host, such as *Escherichia coli*, and then growing the resulting host on an agar medium containing a drug including, for example, kanamycin, chloramphenicol or the like.

The kinds of mutations that can be introduced by the method for performing site-directed mutagenesis of the present invention are not particularly limited. Examples thereof include base substitution, deletion and insertion. Although the size of mutation is not subject to limitation, it is preferable that the length of the mutagenic primer is changed according to the size of mutation. For example, when the size of mutation is about 1 to 3 bases, the length of the mutagenic primer is preferably about 20 bases. When the size of mutation is 4 bases or more, it is preferable that a mutagenic primer of as long as about 30 bases, including about 15 base pairs on each of the 5'-side and 3'-side with respect to the position of desired mutation, is used. It is also desirable that the 3'-terminal of the mutagenic primer is G or C, because the 3'-terminal serves as the origin of polymerase reaction. Taking these conditions into consideration, a mutagenic primer is prepared. It is also possible to evaluate a design and purity of the primer by confirming by means of electrophoresis and the like whether the desired fragment is surely amplified by PCR using the primer. In addition, in the present invention, as to the number of the mutagenic primer, a desired mutation can be introduced by means of a single kind of mutagenic primer. When introducing different mutations at one site, however, a number of mutagenic primers depending on the purposes may be used in mixture to obtain a gene in which each of the desired mutations is introduced by a single operation. For example, when base-substitution site-directed mutagenesis for which alteration of a base at one site from G to A, T or C, respectively, is carried out, genes resulting from introducing mutation of from G to A, T or C, respectively, can be obtained by a single operation by preparing each three kinds of mutagenic primers, and then by using the mutagenic primers in mixture.

In addition, the amber codon reversion primer may be a primer capable of reverting amber codon portions to a wild type and the like, without being particularly limited thereto. For example, when an amber codon is TAG, the amber codon can be reverted by means of a primer prepared so as to alter the TAG to TCG or CTG. It is preferable that the length of the amber codon reversion primer is changed according to the number of amber codons, PCR efficiency, and the like. The length of the amber codon reversion primer is not particularly limited. It is preferable that the length is about 20 bases to about 30 bases. Also, it is desirable that the 3'-terminal of the amber codon, like the mutagenesis primer, is G or C, because the 3'-terminal serves as the origin of polymerase reaction. It is also possible to evaluate a design and purity of the primer by confirming by means of electrophoresis and the like whether the desired fragment is surely amplified by PCR using the primer. In addition, it is recommended that one kind of the amber codon reversion primer is used. When two or more amber codons are present, it is preferable that an amber codon reversion primer is prepared so that those amber codons are reverted by one kind of primer.

The concentration of each of the mutagenic primer and the amber codon reversion primer in PCR is not particularly limited. It is desirable that the respective optimal concentrations during reaction is studied, since when the concentration of each primers is too low, amounts of amplification are decreased, and when the concentration is too high, non-specific reactions are promoted, which in turn may hamper the onset of the specific amplification reaction in some case. Usually, it is preferable that the PCR is carried out within the final concentration range from 0.1 to 1.0 $\mu$M for each primer.

The suppressor-free host, as referred to the present specification, includes but not limited to preferably *Escherichia coli*, for example, *Escherichia coli* MV1184 (manufactured by Takara Shuzo Co., Ltd). Any host can be used, as long as the host lacks suppression ability, and all such hosts are included in the scope of the suppressor-free host as referred in the present specification.

The site-directed mutagenesis by the method of the present invention can, for example, be carried out by the following steps:

(1) A target DNA is inserted into a double-stranded DNA vector having one or more amber codons.

(2) The DNA-inserted vector prepared in the above item (1), a mutagenic primer for introducing a mutation at a desired position on the gene to be mutated, and an amber codon reversion primer for reversion of an amber codon arranged on the strand opposite to the above mutagenic primer are mixed, and then PCR is carried out.

(3) This PCR product is introduced into a suppressor-free (Sup$^0$) host, and a clone having the desired mutation is selected.

By carrying out the above steps, a mutation-introduced gene at the desired position can be obtained efficiently.

In the present invention, since the PCR product resulting from PCR amplification serves as a long-chain primer, the PCR product facilitates the synthesis of full-length DNA during the PCR process. In addition, the PCR product becomes circular when introduced directly into an *Escherichia coli* (in vivo) as a host. In addition, in a case of selection of a clone including a gene introducing a mutation at a desired position, the selection is simplified by a method using a suppression system. Specifically, amber codon reversion can be confirmed simply by introducing the PCR product into a host, e.g., suppressor-free *Escherichia coli*, culturing the resulting host on a medium containing the drug for one of the above-described drug resistance genes, and confirming its growth. In other words, since only an amber codon-reverted clone can be selected, the probability that the grown strain is a clone incorporating a mutation-introduced gene at the desired position.

According to the method of the present invention, an introduction of mutations is possible at any position on the gene to be mutated.

Although ordinary procedures can be used to carry out PCR by the method of the present invention, it is preferred that the cares shown below are considered to avoid erroneous base incorporation by PCR, adenine (A) addition to the 3'-terminal, etc.

(I) The gene to be mutated and inserted into a vector is preferably as short as 2 kbp or less.

(II) The number of PCR cycles is preferably 20 to 30 cycles.

(III) The thermostable DNA polymerase for PCR preferably has a high amplification efficiency and low error rate. For example, the TaKaRa LA PCR Kit (manufactured by Takara Shuzo Co., Ltd.) can be used as the PCR kit. In addition, regarding the thermostable DNA polymerase, it is possible to carry out PCR using TaKaRa Ex Taq (manufactured by Takara Shuzo Co., Ltd.) to achieve high amplification efficiency and low error rate.

Methods for transforming hosts, such as *Escherichia coli*, with PCR product and other hosts include the calcium chloride method [*Journal of Molecular Biology*, 166, pp. 557–580 (1983)] and the electroporation method [*Nucleic Acids Research*, 16, pp. 6127–6145 (1988)]. Regarding screening of the transformants obtained, a clone incorporating a gene of high probability of amber codon reversion, i.e., a gene of high probability of mutation at the desired position, can be selected by culturing the transformants on a medium containing the drug corresponding to one of the above-mentioned drug resistance genes, and then confirming their growth.

Since a simple method for performing site-directed mutagenesis using an amber codon has been made possible by the present invention, it is obvious to those skilled in the art that a termination codon other than the amber codon, i.e., ochre codon or opal codon, can be also applied in place of the amber codon of the present invention. Therefore, methods for performing site-directed mutagenesis using the ochre codon or opal codon in place of the amber codon of the present invention are, as a matter of course, encompassed in the scope of the present invention.

The present invention is hereinafter described in more detail by means of the following examples, but the present invention is not limited to those examples.

EXAMPLE 1

One Base-Substitution Site-Directed Mutagenesis

1. Construction of PKF19kM

Figure 1:
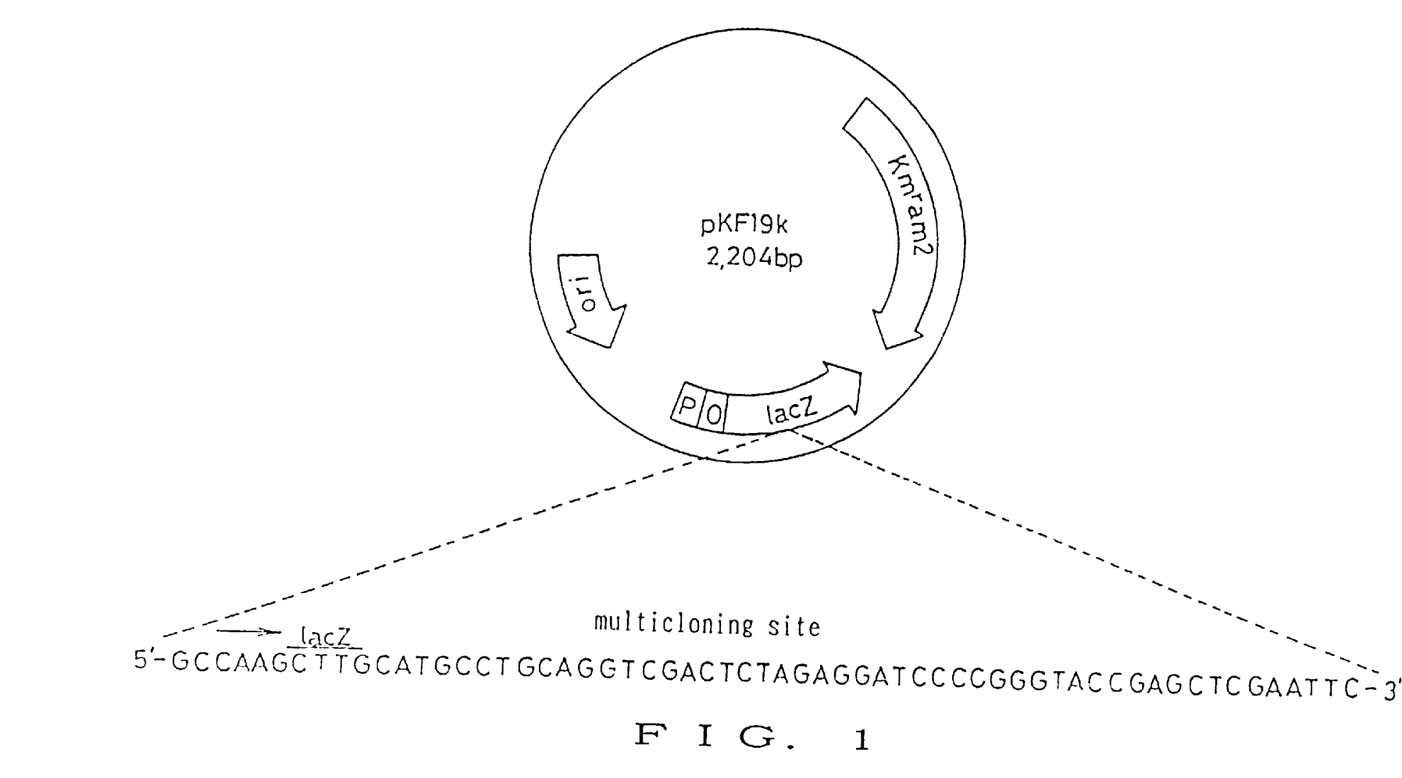
FIG. 1 is a schematic view showing a structure of plasmid pKF19k (SEQ ID NO:8)
Figure 2:
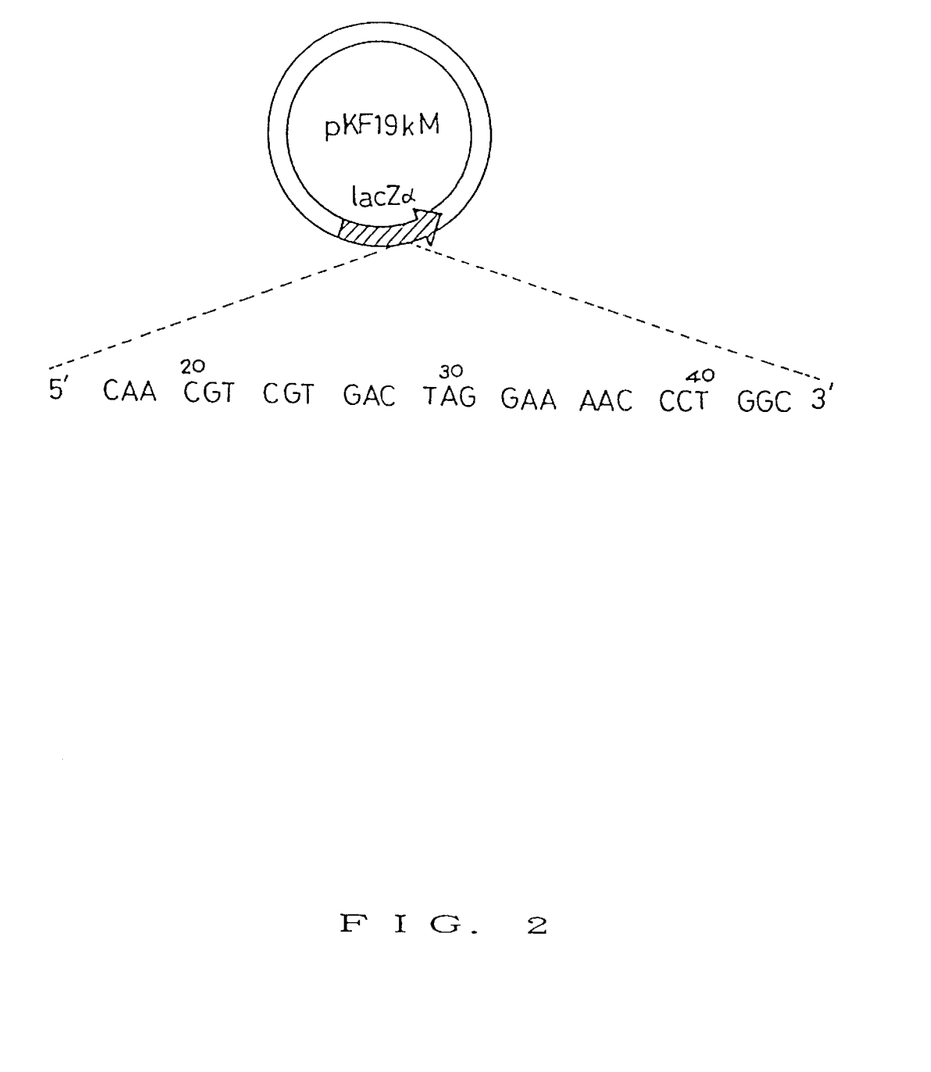
FIG. 2 is a schematic view showing a structure of plasmid PKF19kM (SEQ ID NO:9).

A pKF19kM (FIG. 2) was constructed as the plasmid to be used in the following examples, the pKF19kM resulting from conversion of G to A at a 30th position downstream from the multicloning site in the lacZ' gene in pKF19k (manufactured by Takara Shuzo Co., Ltd., FIG. 1), harboring the kanamycin resistance gene containing two amber codons.

The lacZ' gene exhibits a β-galactosidase activity when lacZ' gene is introduced into a host cell having the lacZΔM15 genotype. Therefore, in the case of the lacZ' gene without base substitution, the resulting grown colonies show a blue color by reacting with 5-bromo-4-chloro-3-indolyl-β-D-galactoside (X-Gal, manufactured by Takara Shuzo Co., Ltd.) as the substrate in the presence of isopropyl-β-D-thiogalactopyranoside (IPTG, manufactured by Takara Shuzo Co., Ltd.). By contrast, the mutant lacZ' gene with base substitution cannot exhibit the inherent activity, so that the resulting grown colonies show a white color.

By utilizing this phenomenon, the efficiency of reversion of the base substitution in the mutant lacZ' gene in pKF19kM to the active gene by site-directed mutagenesis was calculated from the numbers of blue colonies and white colonies.

2. Synthesis of Mutagenic Oligonucleotide (Mutagenic Primer) and Oligonucleotide for Reversion of Double Amber Codons in Kanamycin Resistance Gene (Amber Codon Reversion Primer)

The 5'-terminal phosphorylated oligonucleotide (mut1) as shown by SEQ ID NO: 1 in Sequence Listing was synthesized as a mutagenic oligonucleotide used for reversion of the base substitution site in the mutant lacZ' gene (reversion from A to G). In other words, the mut1 was designed to revert the base substitution by 10th to result in active lacZ' gene.

In addition, the 5'-terminal phosphorylated oligonucleotide as shown by SEQ ID NO: 2 in Sequence Listing was prepared as a primer (KQ2) for reversion of the double amber codons (two amber codons) in the kanamycin resistance gene. Specifically, in pKF19kM, the primer was designed to revert the amber codons (TAG) by TTG at the 3rd to 5th position and CTG at the 9th to 11th position of KQ2.

3. PCR

The composition of a reaction mixture is shown in Table 1. PCR was carried out using a thermal cycler (manufactured by Takara Shuzo Co., Ltd.). The resulting reaction mixture was subjected to ethanol precipitation to desalt and concentrate. Thereafter, the resulting mixture was suspended in 5 μl of sterilized water.

TABLE 1

| pKFl9kM | 5ng |
|---|---|
| primers (mutl and KQ2) | final concentration at 5 pmol each |
| TaKaRa Ex Taq (manufactured by Takara Shuzo Co., Ltd.) | 5U |
| dNTP mixture | final concentration at 200 μM |
| TAPS buffer (pH 9.3, 25° C.) | 25 mM |
| KCl | 50 mM |
| MgCl$_2$ | 2 mM |
| 2-mercaptoethanol | 1 mM |
| | total volume 50 μl (overlaying mineral oil thereon) | note: TAPS= N-Tris(hydroxymethyl)methyl-3-aminopropanesulfonate

A cycle was carried out under the condition of 94° C. for 30 seconds, 55° C. for 2 minutes, and 72° C. for 2 minutes. The above condition was repeated in 20 cycles for Cycle I and 24 cycles for Cycle II. Incidentally, after completion of PCR, each of the PCR products from Cycles I and II was subjected to electrophoresis to confirm that a DNA fragment of a desired size was amplified.

4. Transformation

A suppressor-free *Escherichia coli* MV1184 (manufactured by Takara Shuzo Co., Ltd.) was transformed by the electroporation method using 2 μl of each PCR product after ethanol precipitation. Thereafter, the resulting transformant cells were spread over an LB agar medium [bactotrypton (10 g), bactoyeast extract (5 g), NaCl (5 g), distilled water (1 liter), pH (7.0)] containing kanamycin (50 μg/ml), X-Gal (40 μg/ml) and IPTG (0.2 mM), and the efficiency of site-directed mutagenesis for the clones obtained was calculated. Incidentally, it should be noted that when the mutated portion in the mutant lacZ' gene has been reverted to the active lacz' gene, the resulting colonies show a blue color, and when the mutated portion has not been reverted, the resulting colonies show a white color. The results are shown in Table 2.

TABLE 2

| | blue | white | total | (blue/total) × 100 [%] |
|---|---|---|---|---|
| Cycle I | 586 | 314 | 900 | 65 |
| Cycle II | 2655 | 891 | 3546 | 75 |

In other words, clones with reversion to the active gene by site-directed mutagenesis were obtained at 75% efficiency in Cycle II.

5. Analysis of Site-Directed Mutation Site

A plasmid DNA was prepared by the alkali lysis method for each of four blue colonies obtained in item 4 of Example 1. The base sequence of each of the plasmid DNAs was determined by the dideoxy method, and then a mutation site was analyzed. As a result, G reverted from A was observed at a 30th position downstream of the multicloning site in the lacZ' gene, thereby clearly demonstrating the induction of the site-specific mutation.

EXAMPLE 2

Three Bases- or 6 Bases-Deletion Site-Directed Mutagenesis pKF19k (manufactured by Takara Shuzo Co., Ltd., FIG. 1) was used to delete 3 bases or 6 bases, the pKF19k containing wild type lacZ' gene and kanamycin resistance gene with two amber codons.

1. Synthesis of Mutagenic Oligonucleotide

The 5'-terminal phosphorylated oligonucleotide was synthesized so as to lack a BamHI site and BamHI-EcoRI site in the multicloning site on pKF19k by 3-bases or 6-bases deletion, respectively. An oligonucleotide used in 3-bases deletion (del1) is shown by SEQ ID NO: 3 in Sequence Listing. An oligonucleotide used in 6-bases deletion (del2) is shown by SEQ ID NO: 4 in Sequence Listing. Specifically, del1 was designed to delete bases at the positions between 12th G and 13th C of SEQ ID NO: 3 in Sequence Listing, and del2 was designed to delete bases at the positions between 12th G and 13th T of SEQ ID NO: 4 in Sequence Listing.

2. PCR and Transformation

Thirty cycles of PCR where each of cycles consisted of the conditions of 94° C. for 30 seconds, 55° C. for 2 minutes, and 72° C. for 2 minutes was carried out, by using each of primers del1 and del2 prepared in item 1 in Example 2 and KQ2 primer used in Example 1, according to the composition of Table 1 (in the table, pKF19k was used in place of pKF19kM). The resulting PCR product was then subjected to ethanol precipitation in the same manner as in Example 1. Thereafter, the precipitated PCR product was suspended in 5 μl of sterilized water, and then *Escherichia coli* MV1184 was transformed with 2 μl out of the resulting suspension. Next, the resulting transformants were spread over an LB agar medium containing 50 μl/ml kanamycin, and each of 10 strains was selected from grown colonies. Thereafter, plasmid DNAs were prepared in the same manner as item 5 in Example 1. Confirmation of mutation was carried out by digesting each of the above plasmid DNAs with restriction endonuclease BamHI. In other words, a mutation-introduced plasmid is not digested. The results are shown in Table 3.

TABLE 3

|  | numbers of non-digested clones | numbers of assayed strain | efficiency of mutation (%) |
| --- | --- | --- | --- |
| del1 | 9 | 10 | 90 |
| del2 | 9 | 10 | 90 |

It was confirmed that the mutation was introduced in each of PCR products using primers del1 and del2 at 90% efficiency of mutation, and that 3 bases or 6 bases were deleted in each of PCR products from the results of sequencing.

EXAMPLE 3

Sixty Bases-Deletion Site-Directed Mutagenesis

1. Synthesis of Mutagenic Oligonucleotides

A 5'-terminal phosphorylated oligonucleotide was synthesized so as to lack a whole multicloning site (60 bases) of pKF19k (manufactured by Takara Shuzo Co., Ltd.) by deletion. The oligonucleotide (de13) is shown by SEQ ID NO: 5 in Sequence Listing. In other words, del3 was designed so as to delete a whole multicloning site (60 bases) at the position between 10th T and 11th G of SEQ ID NO: 5 in Sequence Listing.

2. PCR and Transformation

Thirty cycles of PCR where each of cycles consisted of the conditions of 94° C. for 30 seconds, 50° C. for 2 minutes, and 72° C. for 2 minutes were carried out by using primer del3 prepared in item 1 in Example 3 and KQ2 primer used in Example 1 according to the composition of Table 1 (in the table, pKF19k was used in place of pKF19M). The resulting PCR product was then subjected to ethanol precipitation in the same manner as in Example 1. Thereafter, the precipitated PCR product was suspended in 5 μl of sterilized water, and then *Escherichia coli* MV1184 was transformed with 2 μl out of the resulting suspension. Next, the resulting transformants were spread over an LB agar medium containing kanamycin at a concentration of 50 μl/ml, and each of 20 strains was selected from grown colonies. Thereafter, plasmid DNAs were prepared in the same manner as item 5 in Example 1. Confirmation of mutation was carried out by digesting each of the above plasmid DNAs with restriction endonucleases EcoRI and HindIII. In other words, a mutation-introduced plasmid has not been digested. The results are shown in Table 4.

TABLE 4

|  | numbers of non-digested clones | numbers of assayed strain | efficiency of mutation (%) |
| --- | --- | --- | --- |
| del3 | 20 | 20 | 100 |

It was confirmed that the mutation was introduced by PCR using primer del3 at 100% efficiency of mutation, and that a whole multicloning site (60 bases) was deleted from the results of sequencing.

From these results, it was clarified that deletion of bases of a comparably long region could be easily carried out.

EXAMPLE 4

Deletion and Insertion Site-Directed Mutagenesis

1. Synthesis of Mutagenic Oligonucleotides

The 5'-terminal phosphorylated oligonucleotide was synthesized so as to introduce an additional EcoRI site at 100th base downstream from EcoRI site in multicloning site of pKF19k. The oligonucleotide (eco1) is shown by SEQ ID NO: 6 in Sequence Listing. In other words, eco1 was designed so as to delete bases AAT of original sequence corresponding to bases at the positions of from 9th G to 14th C, and to insert an ECORI site, GAATTC.

2. PCR and Transformation

Twenty-four cycles of PCR where each of cycles consisted of the conditions of 94° C. for 30 seconds, 55° C. for 2 minutes, and 72° C. for 2 minutes were carried out, by using primer eco1 prepared in item 1 in Example 4 and KQ2 primer used in Example 1, according to the composition of Table 1 (in the table, pKF19k was used in place of pKF19M). The resulting PCR product was then subjected to ethanol precipitation in the same manner as Example 1. Thereafter, the precipitated PCR product was suspended in 5 μl of sterilized water, and then *Escherichia coli* MV1184 was transformed with 2 μl out of the resulting suspension. Next, the resulting transformants were spread over an LB agar medium containing kanamycin at a concentration of 50 μl/ml, and each of 12 strains was selected from grown colonies. Thereafter, plasmid DNAs were prepared in the same manner as item 5 in Example 1. Confirmation of mutation was carried out by digesting the resulting plasmid with restriction endonuclease EcoRI, and then confirming a DNA fragment of 100 bases by electrophoresis. In other words, a mutation-introduced plasmid has two EcoRI sites at an interval of 100 bases, and the above fragment of 100 bases can be confirmed by digestion with restriction endonuclease EcoRI. The results are shown in Table 5.

TABLE 5

|  | numbers of confirmed fragment of 100 bases | numbers of assayed strain | efficiency of mutation (%) |
| --- | --- | --- | --- |
| eco1 | 12 | 12 | 100 |

It was confirmed that the desired mutant plasmid was obtained by introducing a mutation using primer eco1 at 100% efficiency, and that EcORI site was introduced at the desired site from the results of sequencing.

EXAMPLE 5

Introduction of Mutation into DNA Fragment Ligated to pKF19k

1. Ligation of *Escherichia coli* Plasmid Vector pBR322, to pKF19k

A vector was prepared by digesting pKF19k with restriction endonuclease BamHI, and then incorporating *Escherichia coli* plasmid pBR322 [manufactured by Takara Shuzo Co., Ltd.; *Gene*, 22, pp.277–280 (1983)] having a length of 4361 bases to BamHI site of the above digested pKF19k. The resulting vector was named as pKB101. The site-directed mutagenesis to an insert fragment was made by using the above vector.

2. Synthesis of Mutagenic Oligonucleotide

The 5'-terminal phosphorylated oligonucleotide was synthesized so as to introduce an additional BamHI site at 400th base downstream from BamHI site of pBR322. The oligonucleotide (bam1) is shown by SEQ ID NO: 7 in Sequence Listing. In other words, bam1 was designed so as to substitute the original sequence AGCGCT with BamHI site GGATCC at positions of from 16th G to 21th C of SEQ ID NO: 7 in Sequence Listing.

3. PCR and Transformation

Twenty-five cycles of PCR where each of cycles consisted of the condition of 94° C. for 30 seconds, 55° C. for 30 seconds, and 72° C. for 6 minutes were carried out, by using primer bam1 prepared in item 2 in Example 5 and KQ2 primer used in Example 1 according to the composition of Table 1 (in the table, pKB101 was used in place of pKF19M). The resulting PCR product was then subjected to ethanol precipitation in the same manner as in Example 1. Thereafter, the precipitated PCR product was suspended in 5 μl of sterilized water, and then *Escherichia coli* MV1184 was transformed with 2 μl out of the resulting suspension. Next, the resulting transformants were spread over an LB agar medium containing kanamycin at a concentration of 50 μl/ml, and each of 6 strains was selected from grown colonies. Thereafter, plasmid DNAs were prepared in the same manner as item 5 in Example 1. Confirmation of mutation was carried out by digesting the resulting plasmid with restriction endonuclease BamHI, and then confirming a DNA fragment of 400 bases by electrophoresis. In other words, a mutation-introduced plasmid has two BamHI sites at an interval of 400 bases, and the above fragment of 400 bases can be confirmed by digestion with restriction endonuclease BamHI. The results are shown in Table 6.

TABLE 6

|  | numbers of confirmed fragment of 400 bases | numbers of assayed strain | efficiency of mutation (%) |
|---|---|---|---|
| bam1 | 5 | 6 | 83 |

It was confirmed that the desired mutant plasmid was obtained at 80% or more efficiency for using a DNA fragment ligated to pKF19k, and that BamHI site was introduced at the desired site from the results of sequencing.

EXAMPLE 6
Preparation of Kit for Site-Directed Mutagenesis

A kit for performing site-directed mutagenesis (for 20 runs) was constructed as a set of host *Escherichia coli*, a vector and oligonucleotides used as control (Table 7).

TABLE 7

|  | μl |
|---|---|
| KQ2 primer (for reversion of amber codon; 5 pmil/μl) | 20 |
| multi primer (mutagenic primer; 5 pmol/μl) | 5 |
| pKF19kM (5 ng/μl) | 5 |
| pKF18k and pKF19k (10 OD/ml) | 10 each |
| *Escherichia coli* MV1184 (stored in 10% glycerol solution) | 100 |

Remark: pKF18k and pKF19k being manufactured by Takara Shuzo Co., Ltd.

Incidentally, a kit shown in Table 7 can be combined with a commercially available kit for PCR.

In addition, a kit for performing site-directed mutagenesis (for 20 runs) was constructed, the kit comprising a set of a reaction mixture for carrying out PCR, a dNTP mixture, and thermostable DNA polymerase (Table 8).

TABLE 8

|  | μl |
|---|---|
| TaKaRa Ex Taq (5U/μl; manufactured by Takara Shuzo Co., Ltd.) | 20 |
| 10 × Ex Taq buffer (manufactured by Takara Shuzo Co., Ltd.) | 200 |
| dNTP mixture (2.5 mM each) | 240 |
| KQ2 primer (for amber codon reversion; 5 pmol/μl) | 20 |
| mut1 primer (mutagenic primer; 5 pmol/μl) | 5 |
| pKF19kM (5ng/μl) | 5 |
| pKF18k and pKF19k (10 OD/ml) | 10 each |
| *Escherichia coli* MV1184 (stored in 10% glycerol solution) | 100 |

Remark: pKF18k and pKF19k being manufactured by Takara Shuzo Co., Ltd.

INDUSTRIAL APPLICABILITY

According to the present invention, there can be provided a method for performing site-directed mutagenesis and a kit, which is useful for genetic engineering and protein engineering, more simply and rapidly. By using the method and kit of the present invention, it is possible to efficiently obtain a mutation-introduced gene at a desired position by simply transforming host with a PCR product obtained by PCR.

---

What is claimed is:

1. A method for performing site-directed mutagenesis which comprises the steps of:
   (1) producing a PCR product from a single PCR amplification carried out in a reaction tube, wherein in said tube at least the three following components are present:
      (a) a double-stranded DNA vector having at least one termination codon and having a target DNA fragment for site-directed mutagenesis,
      (b) a selection primer that binds specifically to said at least one termination codon, wherein said selection primer (b) is a termination codon reversion primer that is designed to revert the termination codon to a non-termination codon, and
      (c) a selection primer that binds specifically to said target DNA fragment, wherein said selection primer (c) is a mutagenic primer that is designed to introduce a desired mutation into the target DNA fragment,
   wherein,
      said PCR amplification reaction comprises at least 20 cycles, wherein in an early cycle, a mixture of at least two PCR products are produced:
         (i) a copy of the vector template wherein the desired mutation is present in the target DNA fragment of the copy, and
         (ii) a copy of the vector template wherein the termination codon is reverted to a non- termination codon in the copy,
      and, in a later cycle of said PCR reaction, said selection primer (b) binds to said PCR product (i) to produce a PCR product (iii) having both the desired mutation and the reverted non-termination codon, and
      said selection primer (c) binds to said FCR product (ii) to produce a PCR product (iv) having both the desired mutation and the reverted non-termination codon,
   so that,
      the PCR products (iii) and (iv) bind to the DNA vector and serve as a long-chain PCR primer for the amplification of a full-length copy of said DNA vector that possesses both the desired mutation and the reverted non-termination codon, within said single PCR amplification; and
   (2) transforming a suppressor-free (Sup$^0$) host with the PCR product of step (1), thereby directly obtaining a desired mutant.

2. The method of claim 1, further comprising concentrating the PCR product of step (1) into a precipitate prior to step (2).

3. The method of claim 1, wherein when the size of the desired mutation is about 1 to 3 nucleotide bases and the length of said selection primer (c) that specifically binds to said target DNA fragment is at least 20 nucleotide bases.

4. The method of claim 1, wherein when the size of the desired mutation is at least 4 nucleotide bases and the length of said selection primer that specifically binds to said target DNA fragment is at least 30 nucleotide bases.

5. The method of claim 1, wherein the 3' terminal nucleotide of said selection primer (c) and/or said selection primer (b) is G or C.

6. The method of claim wherein 1, the length of the selection primer (b) is at least 20 bases.

7. The method of claim 1, wherein the double-stranded DNA vector has two termination codons.

8. The method of claim 1, wherein the double-stranded DNA vector further comprises a gene for drug-resistance.

9. The method of claim 8, wherein the gene for drug-resistance encodes at least one termination codon.

10. The method of claim 1, wherein said selection primer (b) binds to the DNA strand opposite from the DNA strand to which said selection primer (c) binds.

11. The method of claim 1, wherein said termination codon reversion primer is designed to revert the TAG to TCG or CTG.

12. The method of claim 1, wherein the target DNA fragment is at most 2 kbp.

13. The method of claim 1, wherein said termination codon is an amber codon.

14. The method of claim 1, wherein said termination codon is an ochre codon.

15. The method of claim 1, wherein said termination codon is an opal codon.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 1
gggttttccc agtcacgacg        20

<210> SEQ ID NO 2
<211> LENGTH: 20

<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
gattgcgcct gagcgagacg                                                     20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cggtacccgg ggctctagag tcg                                                 23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
cggtacccgg ggtagagtcg acc                                                 23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gacggccagt gtaatcatgg                                                     20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gctggcgtga attcagcgaa gagg                                                24

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ccgaaaatga cccagggatc cgccggcacc                                          30

<210> SEQ ID NO 8
<211> LENGTH: 60
<212> TYPE: DNA

-continued

```
<213> ORGANISM: Artificial Sequence
<220> FEATURE:
<223> OTHER INFORMATION: Description of Artificial Sequence: Synthetic
      DNA

<400> SEQUENCE: 8
gccaagcttg catgcctgca ggtcgactct agaggatccc cgggtaccga gctcgaattc          60

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
caacgtcgtg actaggaaaa ccctggc                                              27
```